United States Patent
Simpson et al.

(10) Patent No.: US 8,030,077 B2
(45) Date of Patent: Oct. 4, 2011

(54) NON-LINEAR OPTICAL IMAGING OF PROTEIN CRYSTALS

(75) Inventors: Garth J. Simpson, West Lafayette, IN (US); Ronald D. Wampler, Midvale, UT (US); David J. Kissick, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 12/537,775

(22) Filed: Aug. 7, 2009

(65) Prior Publication Data

US 2010/0031748 A1  Feb. 11, 2010

Related U.S. Application Data

(60) Provisional application No. 61/087,216, filed on Aug. 8, 2008.

(51) Int. Cl.
*G01N 21/88* (2006.01)
*G01N 21/63* (2006.01)
*G01N 33/483* (2006.01)

(52) U.S. Cl. .................. 436/4; 356/30; 436/86; 436/87; 436/171

(58) Field of Classification Search .................. 356/30; 436/4, 86–87, 181, 171
See application file for complete search history.

(56) References Cited

OTHER PUBLICATIONS

LeCaptain, D. J. et al, Journal of Crystal Growth 1999, 203, 564-569.*
Chu, S.-W. et al, Journal of Microscopy 2002, 208, 190-200.*
Mohler, W. et al, Methods 2003, 29, 97-109.*
Strachan, C. J. et al, Journal of Pharmaceutical Sciences 2004, 93, 733-742.*
Moreno, N. et al, Micron 2004, 35, 721-724.*
Fischer, P. et al, Chirality 2005, 17, 421-437.*
Rawle, C. B. et al, Journal of Pharmaceutical Sciences 2006, 95, 761-768.*
Blundell, T. L. et al., "High-Throughput Crystallography for Lead Discovery in Drug Design" *Nature Reviews Drug Discovery* 2002, 1, 45-54.
Bodenstaff, E. R. et al., "The prospects of protein nanocrystallography" *Acta Crystallographica D* 2002, D58, 1901-1906.
Cumbaa, C. A.;et al., "Automatic classification of sub-microlitre protein-crystallization trials in 1536-well plates." *Acta Crystallographica D* 2003, D59, 1619-1627.
Dailey, C. A. et al., "The General Failure of Kleinman Symmetry in Practical Nonlinear Optical Applications" *Chem. Phys. Lett.* 2004, 390, 8-13.
Drahl, C. "Spotting Nascent Protein Crystals—Optical technique reduces background noise and could cut screening times and costs" *Chem. & Eng. News* 2008, p. 11.
Echalier, A. et al., "Assessing crystallization droplets using birefringence" *Acta Crystallographica D* 2004, D60, 696-702.
Forsythe, E. et al., "Trace fluorescent labeling for high-throughput crystallography" *Acta Crystallographica D* 2006, D62, 339-346.
Groves, M. R. et al., "A method for the general identification of protein crystals in crystallization experiments using a noncovalent fluorescent dye" *Acta Crystallographica D* 2007, D63, 526-535.
Kleinman, D. A., "Nonlinear dielectric polarization in optical media" *Phys. Rev.* 1962, 126, 1977-1979.
Moad, A. J. et al., "Visualization and data analysis software for nonlinear optics" *J. Comput. Chem.* 2007, 28, 1996-2002.

(Continued)

*Primary Examiner* — Arlen Soderquist
(74) *Attorney, Agent, or Firm* — Brinks Hofer Gilson & Lione (57) ABSTRACT

Methods for detecting and evaluating the quality of protein crystals are provided comprising subjecting a sample to second order non-linear optical imaging and detecting the second harmonic generation signal.

20 Claims, 3 Drawing Sheets

OTHER PUBLICATIONS

Santarsiero, B. D. et al., An approach to rapid protein crystallization using nanodroplets. *J. Appl. Crystallography* 2002, 35, 278-281.

Spraggon, G. et al., Computational analysis of crystallization trials. *Acta Crystallographica D* 2002, D58, 1915-1923.

Wampler, R. D et al. Molecular Design Strategies for Optimizing the Nonlinear Optical Properties of Chiral Crystals. *Cryst. Growth and Design* 2008, 8 (8), pp. 2589-2594.

Wampler, R.D. et al. "Selective Detection of Protein Crystals by Second Harmonic Microscopy" *J. Am. Chem. Soc.* 2008, 130. 14076-14077.

Williams, R. M. et al.., Interpreting second-harmonic generation images of collagen I fibrils. *Biophys. J.* 2005, 88, 1377-1386.

Zheng, B. et al., Screening of protein crystallization conditions on a microfluidic chip using nanoliter-size droplets. *J. Am. Chem. Soc.* 2003, 125, 11170-11171.

\* cited by examiner

NON-LINEAR OPTICAL IMAGING OF PROTEIN CRYSTALS

RELATED APPLICATIONS

The present patent document claims the benefit of the filing date under 35 U.S.C. §119(e) of Provisional U.S. Patent Application Ser. No. 61/087,216, filed Aug. 8, 2008 which is hereby incorporated by reference.

FEDERALLY SPONSORED RESEARCH OR DEVELOPMENT

The present invention described herein was supported at least in part by the National Science Foundation (Grants CHE-0640549, MRI:ID-0722558). The government may have certain rights in the invention.

BACKGROUND

The present invention generally relates to protein crystals and methods for identifying diffraction-quality protein crystals.

In proteins, structure dictates function. The major cost in terms of time and expense in protein structure determination by x-ray crystallography often rests in the identification of conditions for generating diffraction-quality protein crystals. With the human genome now sequenced, efforts over the last decade have shifted increasingly toward structural characterization of the proteins encoded by the genome, primarily through diffraction analysis. Major bottlenecks in this effort rest in the time and expense associated with isolating and purifying functional proteins, and identifying appropriate conditions for growth of diffraction-quality crystals. Several high-throughput platforms for screening protein crystallization conditions have been developed with reasonably good success. (Cumbaa, C. A.; Lauricella, A.; Fehrman, N.; Ceatch, C.; Collins, R. W.; Luft, J.; DeTitta, G.; Jurisica, I., Automatic classification of sub-microlitre protein-crystallization trials in 1536-well plates. *Acta Crystallographica D* 2003, D59, 1619-1627. Spraggon, G.; Lesley, S. A.; Kreusch, A.; Priestle, J. P., Computational analysis of crystallization trials. *Acta Crystallographica D* 2002, D58, 1915-1923. Echalier, A.; Glazer, R. L.; Fülöp, B.; Deday, M. A., Assessing crystallization droplets using birefringence. *Acta Crystallographica D* 2004, D60, 696-702. Bodenstaff, E. R.; Hoedemaeker, F. J.; Kuil, M. E.; de Vrind, H. P. M.; Abrahams, J. P., The prospects of protein nanocrystallography. *Acta Crystallographica D* 2002, D58, 1901-1906. Blundell, T. L.; Jhoti, H.; Abell, C., High-Throughput Crystallography for Lead Discovery in Drug Design. *Nature Reviews Drug Discovery* 2002, 1, 45-54. Zheng, B.; Roach, L. S.; Ismagilov, R. F., Screening of protein crystallization conditions on a microfluidic chip using nanoliter-size droplets. *J. Am. Chem. Soc.* 2003, 125, 11170-11171. Santarsiero, B. D.; Yegian, D. T.; Lee, C. C.; Spraggon, G.; Gu, J.; Scheibe, D.; Uber, D. C.; Cornell, E. W.; Nordmeyer, R. A.; Kolbe, W. F.; Jin, J.; Jones, A. L.; Jaklevic, J. M.; Shchultz, P. G.; Stevens, R. C., An approach to rapid protein crystallization using nanodroplets. *J. Appl. Crystallography* 2002, 35, 278-281.) However, the number of conditions that can be sampled in any screening measurement is ultimately dictated by the total quantity of initial purified protein and the smallest detectable protein crystal. Reduction in the detection limits for protein crystallization can potentially reduce both the time required for performing an assay of conditions and the total amount of protein consumed. The challenges associated with early detection of protein crystallization are numerous. Optical detection approaches are arguably most directly compatible with diverse crystallization platforms and enable continuous monitoring of the same sample at multiple time-points. Commercially available approaches based on image analysis (Cumbaa, C. A.; Lauricella, A.; Fehrman, N.; Ceatch, C.; Collins, R. W.; Luft, J.; DeTitta, G.; Jurisica, I., Automatic classification of sub-microlitre protein-crystallization trials in 1536-well plates. *Acta Crystallographica D* 2003, D59, 1619-1627. Spraggon, G.; Lesley, S. A.; Kreusch, A.; Priestle, J. P., Computational analysis of crystallization trials. *Acta Crystallographica D* 2002, D58, 1915-1923) or birefringence (Echalier, A.; Glazer, R. L.; Fülöp, B.; Deday, M. A., Assessing crystallization droplets using birefringence. *Acta Crystallographica D* 2004, D60, 696-702) are limited to crystals with dimensions spanning at least several µm. Incorporating a fluorophore by doping (Groves, M. R.; Müller, I. B.; Kreplin, X.; Müller-Dieckmann, J., A method for the general identification of protein crystals in crystallization experiments using a noncovalent fluorescent dye. *Acta Crystallographica D* 2007, D63, 526-535.) or covalent attachment (Forsythe, E.; Achari, A.; Pusey, M. L., Trace fluorescent labeling for high-throughput crystallography. *Acta Crystallographica D* 2006, D62, 339-346.) can improve on these detection limits, but also introduces a significant background signal from solvated dye molecules and amorphous aggregates.

All of these previously established methods suffer from the inability to easily detect sub-diffraction limited crystals and to discriminate between the formation of protein crystals versus the localized deposition of amorphous protein aggregates. What is needed is a sensitive and selective detection method for protein crystals and crystallization, with detection limits for the onset of crystallization corresponding to crystal dimensions well below the optical diffraction-limit.

BRIEF SUMMARY

The unique selection rules of second harmonic generation (SHG) microscopy enable sensitive and selective imaging of protein microcrystals with negligible contributions from solvated proteins or amorphous protein aggregates thus enabling the identification of conditions for generating diffraction-quality protein crystals. In addition to being sensitive and highly selective, second order nonlinear optical imaging of chiral crystals (SONICC) is directly compatibility with virtually all common protein crystallization platforms.

In one embodiment, a method of detecting a protein crystal is provided. The method comprises subjecting a sample comprising protein in solid form to second order non-linear optical imaging; and detecting a second harmonic generation signal produced by a protein crystal. The protein crystal has a diameter of less than about 1 micron in some aspects and less than about 100 nm in other aspects. The method may comprise illuminating the sample with a pulsed laser light. The sample may be formed from a crystallization experiment.

In another embodiment, a method for evaluating protein crystal quality is provided. The method comprises subjecting a sample comprising a protein crystal to second order non-linear optical imaging; detecting a second harmonic generation signal produced by the protein crystal; comparing a forward second harmonic generated signal and a backward second harmonic generated signal of the protein crystal, and selecting a protein crystal exhibiting a predominately forward scattering for use in crystallography. The forward second harmonic generated signal may be between about 4 times and about 6 times greater than the backward second harmonic generated signal. The diameter of the protein crystal may be larger than 1 micron, less than about 1 micron, or less than 100 nm. The method may further comprise illuminating the sample with a pulsed laser light.

In another embodiment, a method for evaluating protein crystal quality comprises subjecting a sample comprising a protein crystal to second order non-linear optical imaging; illuminating the protein crystal with a pulsed laser beam at a first incidence angle; detecting a second harmonic generation signal produced by the protein crystal at the first incidence angle; rotating the protein crystal to a second incidence; detecting a second harmonic generation signal produced by the protein crystal at the second incidence angle; and comparing the second harmonic generation signal produced by the protein crystal at the first and second incidence angle. The method may further comprise measuring the intensity of the second harmonic generation signal produced by the protein crystal at the first incidence angle; measuring the intensity of the second harmonic generation signal produced by the protein crystal at the second incidence angle; comparing the intensity of the second harmonic generation signal produced by the protein crystal at the first and second incidence angle; selecting a protein crystal exhibiting a lower minimum intensity for use in crystallography. The diameter of the protein crystal may be larger than 1 micron, less than about 1 micron, or less than 100 nm. The methods may further comprise illuminating the sample with a pulsed laser light.

In yet another embodiment, a method for evaluating a crystallization experiment is provided. The method comprises subjecting a protein crystallization experiment to second order non-linear optical imaging; and using one or more second harmonic generation signals to evaluate whether protein crystal is present in the crystallization experiment. The method may further comprise illuminating the crystallization experiment with a pulsed laser beam. The protein crystal may have a diameter of less than about 1 micron.

In another embodiment, a method of identifying protein crystals suitable for x-ray crystallography is provided. The method comprises subjecting a sample containing specimens of protein crystals and amorphous protein aggregates to second order non-linear optical imaging, comparing the forward and backward second harmonic generated signal for each specimen, and selecting any specimen exhibiting a predominately forward scattering for use in subsequent x-ray crystallography.

Other features and advantages of the present invention will become apparent to those skilled in the art from the following disclosure of preferred embodiments of the present invention exemplifying the best mode of practicing the invention. The following disclosure references the accompanying drawings illustrating the preferred embodiments.

DETAILED DESCRIPTION

Abbreviations and Definitions

When describing the methods of this invention, the following terms have the following meanings, unless otherwise indicated.

Crystal or crystalline solid refers to a solid material whose constituent atoms, molecules, or ions are arranged in an orderly repeating pattern extending in all three spatial dimensions.

Crystallography refers to the scientific study of crystals, crystal formation, and the science of determining the arrangement of atoms in crystalline solids. Protein refers to a chiral organic compound made of natural or unnatural amino acids arranged in a chain and linked by amide bonds.

GFP refers to green fluorescent protein.
NLO refers to non-linear optics.
SHG refers to second harmonic generation microscopy.
SONICC refers to second order non-linear optical imaging of chiral crystals.
TPEF refers to two-photon excited fluorescence.

Methods

The present invention provides second order non-linear optical imaging of chiral crystals (SONICC) as a sensitive and selective detection method for protein crystals and crystallization, with detection limits for the onset of crystallization corresponding to crystal dimensions well below the optical diffraction-limit. Whereas the symmetry requirements intrinsic to second-order nonlinear optical methods demand that second harmonic generation microscopy (SHG) is electric dipole forbidden in isotropic, unoriented media and in centrosymmetric crystal classes, all protein crystals are chiral and fall into a relatively small set of crystal classes that are necessarily symmetry-allowed for SHG, including for example crystal classes 2, 222 and the like. As such, protein crystals may be detected by second order non-linear optical imaging including, for example, second harmonic generation microscopy.

A sample that comprises a protein crystal or potentially comprises a protein crystal is subjected to second order non-linear optical imaging. The sample may be any suitable sample including an isolated protein crystal, a protein in solid form, a product of a protein crystallization experiment, and the like. A protein in solid form may include amorphous or crystalline protein, or a combination thereof. Because achiral crystals are not responsive to second order non-linear optical imaging, the sample may comprise achiral crystals including for example inorganic salts without interfering with the imaging of the protein crystal. The present method may be used to distinguish a protein crystal from an achiral crystal including an achiral inorganic salt because the protein crystal will produce a second harmonic generation signal whereas the achiral crystal will not. In addition, second order non-linear optical imaging may be performed on virtually any optically accessible platform for crystallization, addressing a key bottleneck in the procedure for determining protein structure.

Subjecting a sample to second order non-linear optical imaging may be performed by any suitable method known to one skilled in the art. The sample is illuminated with a pulsed laser light or beam which provides short pulses of high peak power. The pulsed laser may be a modelocked, Q-switching or pulsed pumping laser, preferably a modelocked laser. The laser may be pulsed on the order of nanoseconds, picoseconds or femtoseconds, preferably less than one nanosecond, more preferably less than one picosecond, even more preferably between about 500 and about 10 femtoseconds.

Second harmonic generation or frequency doubling, generates light with a doubled frequency (half the wavelength) the source light. Thus, the frequency of the light emitted from the protein crystal is twice that of the source light and the wavelength of the emitted light is half that of the source light. In order to aid in detection of the emitted light, the emitted light may be in the visible light region, for example from about 380 to 750 nm. When the source of coherent light is a 1064-nm Nd:YAG laser, frequency doubling will result in visible light with a wavelength of 532 nm (green). When the source of coherent light is a 800-nm Ti:sapphire laser, frequency doubling results visible light with a wavelengths of 400 nm (violet).

Second order non-linear optical imaging may be used for the sensitive detection of nascent protein crystals, and offers significant advantages compared to alternative methods currently used in automated high throughput crystallization screenings including limits of detection and selectivity. Traditional high-throughput crystal screening methods can only detect protein crystals that are at least micrometer-sized. Second order non-linear optical imaging may be used to detect protein crystals less than a micrometer in diameter. Even under low magnification, second order non-linear optical imaging yields a signal to noise ratio of 3 for chiral crystals of 100 nm in diameter. This value corresponds to the detection of protein crystals approximately 1/20 the diameter of the beam waist in the focal plane. The diameter of the protein crystal may be less than about one micron, preferably less than about 500 nm, more preferably less than about 100 nm. Given that second harmonic generation scales with the fourth power of the beam waist, significant reductions in the detection limits may be possible under higher magnification.

In one embodiment, a method for evaluating protein crystal quality is provided. The forward second harmonic generated signal and the backward second harmonic generated signal which are generated by subjecting the protein crystal to second order non-linear optical imaging may be detected and measured by any suitable method known to one skilled in the art. By comparing the forward and backward second harmonic generated signals, protein crystals suitable for crystallography and diffraction crystallography may be identified. Protein crystals which exhibit predominantly forward scattering in comparison to backward scattering are suitable for diffraction crystallography. Diffraction crystallography includes X-ray and electron diffraction. Protein crystals suitable for diffraction crystallography have a forward second harmonic generated signal greater than the backward second harmonic generated, preferably between about 4 times and about 6 times greater, more preferably about 5 times greater.

Given the coherent nature of second harmonic generation microscopy, the orientation of the crystal relative to the axis of the beam has a significant impact on the efficiency of second harmonic generation. By comparing the second harmonic generation signal at various incidence angles for a given protein crystal, the quality of the protein crystal may be assessed. The intensity of the second harmonic generation signal at the various incidence angles may be measured. Protein crystals with lower minimum intensities are preferred for diffraction crystallography.

EXAMPLES

Conventional methods for protein crystal detection include fluorescence microscopy which has limited application for protein crystal detection because it requires that the protein be a fluorophore or that the crystal be doped with a fluorophore. In contrast, second harmonic generation is not dependent upon the presence of a fluorophore and therefore is more broadly applicable to protein crystals detection.

Figure 1:
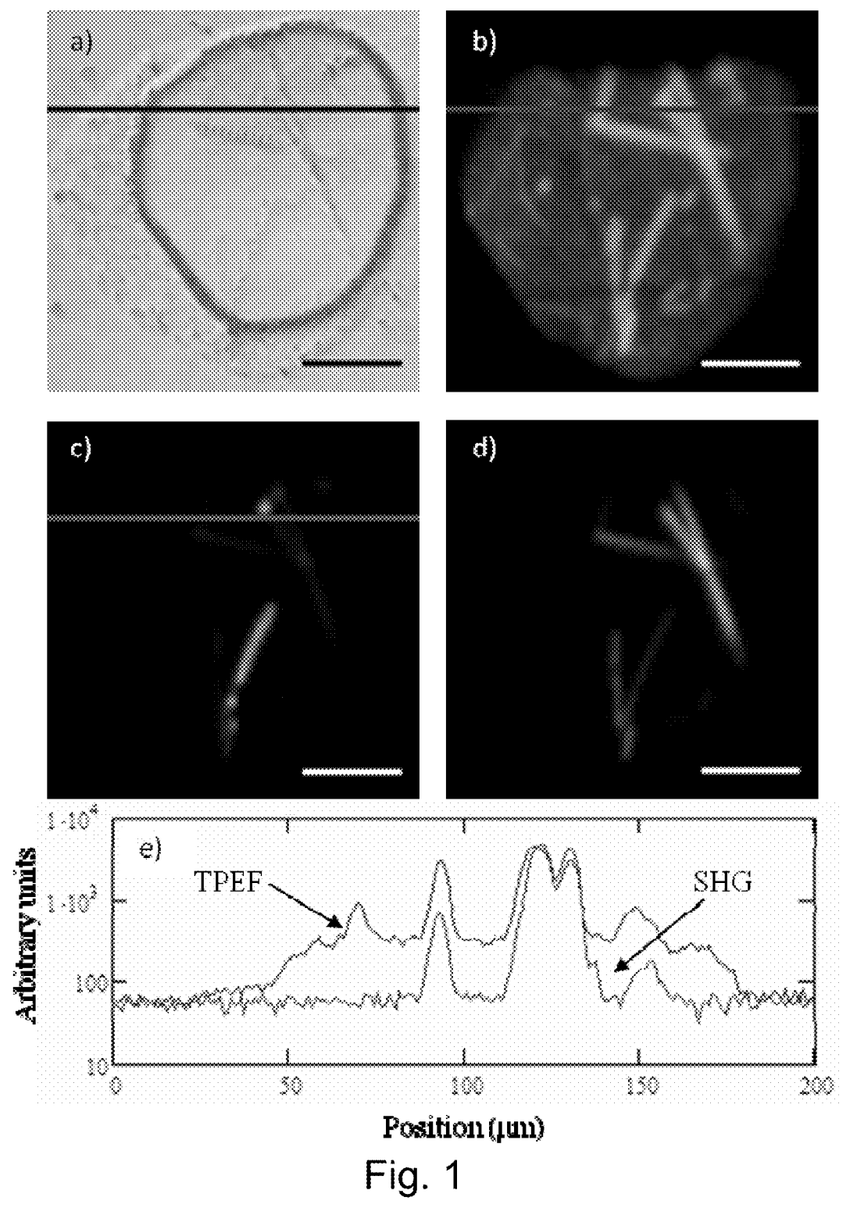
FIG. 1 is a comparison of imaging techniques for GFP crystals; bright field (a), epi-detected TPEF (b), epi-detected SHG (c), transmitted SHG (d), and a line scan on a log scale for TPEF (green) and SHG (blue) (e). Scale bar: 50 µm.

For example, a direct comparison of second harmonic generation microscopy with a conventional method such as fluorescence microscopy for protein crystal detection was made using green fluorescent protein (GFP) as a model system. GFP allows for simultaneous two-photon excited fluorescence (TPEF) and second harmonic gernation by nature of the intrinsic fluorophore. In addition, because GFP is a fluorophore itself, fluorescence microscopy of GFP crystals represent the extreme lower detection limit for methods based on assessing crystallization by doping with fluorophores, corresponding to the theoretical maximum of 100% incorporation. FIG. 1 shows representative results comparing TPEF and SHG images for GFP crystals. Inspection of both the raw images and a corresponding cross-section through a single line scan reveals that the peak intensities measured for both TPEF and SHG are comparable, with the most notable difference being the much higher background in the case of TPEF.

Without wishing to be bound by theory, the increase in the background in TPEF relative to SHG is thought to be due to the nature of the fundamental differences in the symmetry requirements of the two measurements. Coherent second harmonic generation arises from an "orientation selection rule", and is electric-dipole forbidden in media lacking orientational order extending over distances larger than the optical wavelength. In contrast, the photons generated through TPEF can be considered as arising from individual emission events, and are therefore neither highly directional nor coherently connected.

Figure 2:
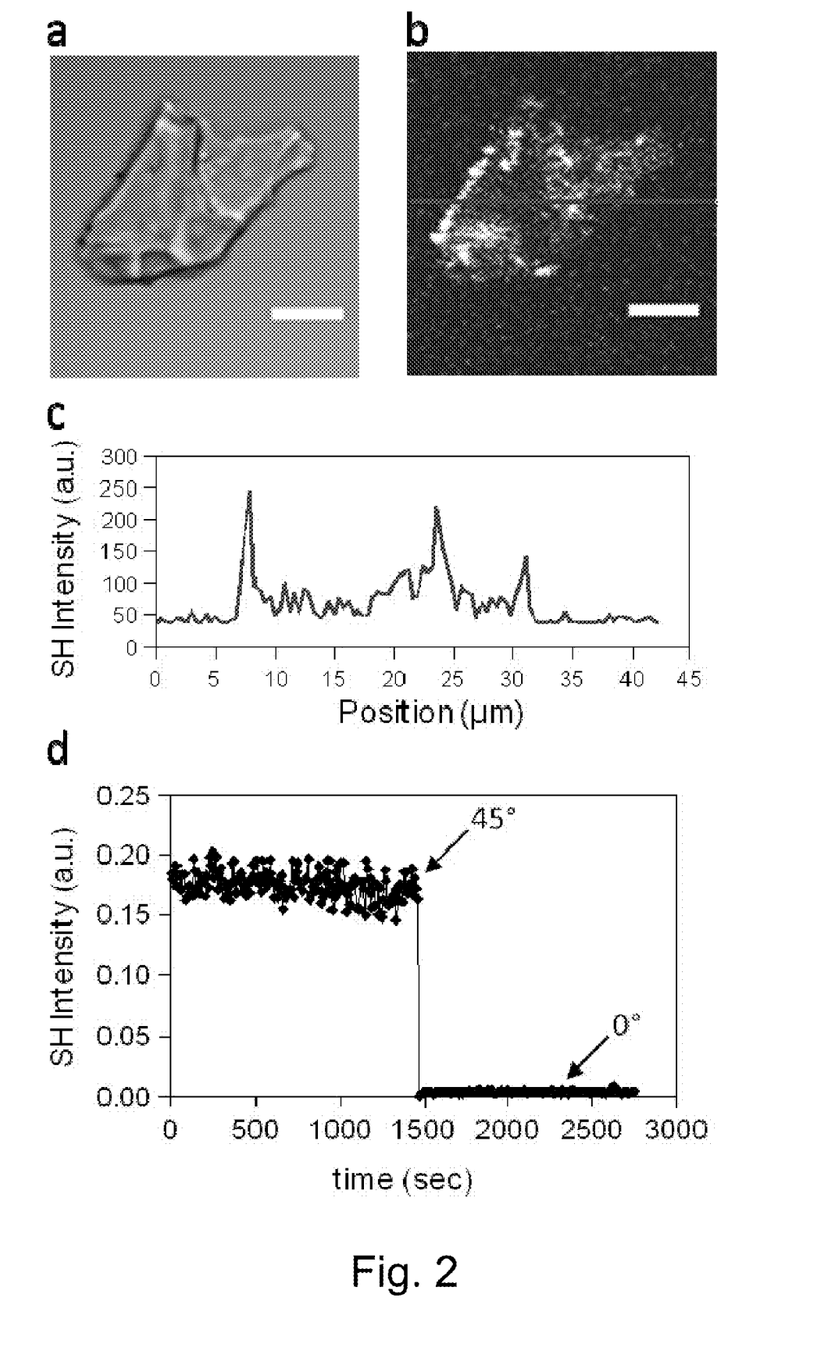
FIG. 2 is a bright field image of lysozyme crystals (a) and the corresponding epi-detected SHG micrograph (b). A representative line scan is shown in (c). The angle-dependence of the SHG is shown in (d), highlighting the difference in SHG for angles of incidence of 45° and 0° (i.e., normal to slide surface). Scale bar: 15 µm.

Although GFP provides a convenient platform for direct comparison of SHG and fluorescence-based approaches, the majority of proteins do not contain efficient intrinsic fluorophores. The generality of SHG microscopy for detection of protein crystals is exemplified through measurements of lysozyme crystals. Bright-field and epi-detected SHG images of lysozyme crystals are shown in FIG. 2 along with measurements acquired using a long focal length lens of a similarly prepared sample. As shown in FIG. 2, unlabeled lysozyme crystals probed by SHG microscopy produce easily detectable signals. Furthermore, the SHG activity is quite stable, changing negligibly over ~30 minutes of continuous data acquisition from the same location in a signal crystal (FIG. 2d).

The orientation of the crystal relative to the axis of the beam impacts the efficiency of SHG. Measurements of a single crystal performed normal to the substrate surface (presumably commensurate with the crystallographic c-axis) resulted in a reduction in the SHG intensity compared to measurements of the same crystal acquired at an angle of incidence of 45° (FIG. 2d).

The size of the protein crystal may also impact the efficiency of SHG. In microscopy studies, relatively large pristine lysozyme crystals were only weakly SHG active when measured in an epi-detected microscopy configuration with the focal plane parallel to the surface plane. The size of the protein crystal is preferably smaller than the wavelength of the light source.

$P4_32_12$ lysozyme crystals may be prepared under the batch crystallization conditions (McPherson, A., *Crystallization of biological macromolecules*. Cold Spring Harbor Laboratory Press: New York, 1999) and fall into a relatively high symmetry class containing a 4-fold screw axis and an orthogonal 2-fold screw axis, which collectively reduce the net SHG activity. Theoretical calculations were performed using NLOPredict (Moad, A. J.; Moad, C. W.; Perry, J. M.; Wampler, R. D.; Begue, N. J.; Shen, T.; Goeken, G. S.; Heiland, R.; Simpson, G., J., NLOPredict: Visualization and data analysis software for nonlinear optics. *J. Comput. Chem.* 2007, 28, 1996-2002) to estimate the overall SHG activity of the lysozyme crystals. Upon performing the orientational averaging associated with the protein structure and the symmetry operations of the crystal and considering only the amide chromophores, the net NLO activity of crystalline lysozyme (evaluated by the squared norm of the $\beta^{(2)}$ tensor) was calculated to be less than 1% of what would be expected for highly oriented δ-function distribution of lysozyme molecules. The net residual NLO response of lysozyme per protein molecule within the crystal is roughly equivalent to about 1.3 amide chromophores upon orientational averaging. Even so, lysozyme crystals generate strong SHG responses in SONICC measurements.

Protein crystals with lower symmetry are expected to generate even stronger SHG responses in SONICC measurements. Roughly half of all protein crystals currently listed within the Protein Data Bank belong to the 222 and 2 crystal classes. Protein crystals in these are expected to generate significantly larger SHG-activity by nature of their lower symmetry. (Wampler, R. D.; Begue, N. J.; Simpson, G., J., Molecular Design Strategies for Optimizing the Nonlinear Optical Properties of Chiral Crystals. *Cryst. Growth and Design* 2008, 8 (8), pp 2589-2594)

Experimental

The minimum crystal size detected by SHG was estimated by monitoring the transmitted and epi-detected SHG generated during crystallization of lysine by slow evaporation. For a particle thickness much less than the wavelength of light, the efficiency of generating forward versus backward propagating SHG is nearly equal. However, when the physical thickness of the SHG-active crystals generated upon evaporation reach a thickness approaching roughly λ/2, the ratio of forward to backward generated SHG transitions to predominantly forward scattering.(Williams, R. M.; Zipfel, W. R.; Webb, W. W., Interpreting second-harmonic generation images of collagen I fibrils. *Biophys. J.* 2005, 88, 1377-1386) Consequently, the transition point at which the ratio of the F/B ratio departs from a value of ~1 serves as a built-in "ruler" for estimation of the particle size. The signal to noise ratio (S/N) of ~9 at this transition point corresponds to a particle with a diameter of ~200 nm. Assuming that the signal scales with the volume of monomers within the crystal lattice for a spherical particle and Poisson noise and including contributions from dark counts, the cubic dependence of the signal on volume puts the minimum detection size for this configuration at ~100 nm for a S/N of 3. This estimate for the detection limit is approximately 1/20 the beam waist used in the measurements.

SHG microscopy measurements of lysozyme crystals.

The regions of high image contrast in SHG microscopy measurements of lysozyme crystals consisted primarily of polycrystalline conglomerates and small optical scattering centers within the lysozyme lattice which may be attributable to lattice defects. Relatively large, pristine crystals generated weaker second harmonic generation-activity. Three effects were considered for influencing the overall strength of the SH response arising from lysozyme crystals: i) the inherit SH activity of the protein crystals itself; ii) the angle of incidence of the laser probe relatively to the crystallographic axes; iii) the interplay between the size of the crystals and the geometry used to collect the SH signals [i.e., the forward or backward (epi) direction].

The net NLO tensor for crystalline lysozyme was estimated by using NLOPredict in combination with quantum chemical calculations of the amide chromophores. NLOPredict is a program designed in part to predict the net tensors of proteins and protein crystals through orientational averaging of the different chromophores inherent in the protein structure (e.g., amide units). (Moad, A. J.; Moad, C. W.; Perry, J. M.; Wampler, R. D.; Begue, N. J.; Shen, T.; Goeken, G. S.; Heiland, R.; Simpson, G., J., NLOPredict: Visualization and data analysis software for nonlinear optics. *J. Comput. Chem.* 2007, 28, 1996-2002) The known structure for the $P4_32_12$ polymorph expected under these experimental conditions was used in the predictions along with the nonresonant tensor for the amide monomer, calculated by a double sum-over-states approach including 100 excited states to achieve convergence. It was assumed in the calculations that the amide chromophores dominate the net NLO response of lysozyme by nature of their relatively high number density. Including contributions from the aromatic side-chains may increase the net second harmonic generation activity predicted for lysozyme. Based on this approach, orientational averaging associated with the symmetry operations of the crystal significantly reduces the net NLO activity of lysozyme crystals. The squared norm (i.e., the sum of the squares of each tensor element) of a lysozyme monomer is approximately 154 times that of a single amide monomer, but the symmetry operations of the lattice reduce the net contributions per lysozyme to just 1.3 times that of a single amide monomer. This high degree of cancellation arises primarily by the presence of the 4-fold screw axis combined with the orthogonal 2-fold screw axis, collectively leaving only the Kleinman-disallowed chiral contributions remaining. (Kleinman, D. A., Nonlinear dielectric polarization in optical media. *Phys. Rev.* 1962, 126, 1977-1979. Dailey, C. A.; Burke, B. J.; Simpson, G. J., The General Failure of Kleinman Symmetry in Practical Nonlinear Optical Applications. *Chem. Phys. Lett.* 2004, 390, 8-13. Wampler, R. D.; Begue, N. J.; Simpson, G., J., Molecular Design Strategies for Optimizing the Nonlinear Optical Properties of Chiral Crystals. *Cryst. Growth and Design* 2008, 8 (8), pp 2589-2594) Inspection of the contents within the protein crystallographic data bank suggests that ~95% of protein crystals fall into symmetry classes that do not contain a 4-fold or higher rotational axis, such that the net second harmonic generation activities of most protein systems can be reasonably expected to far exceed those of this lysozyme polymorph.

Figure 3:
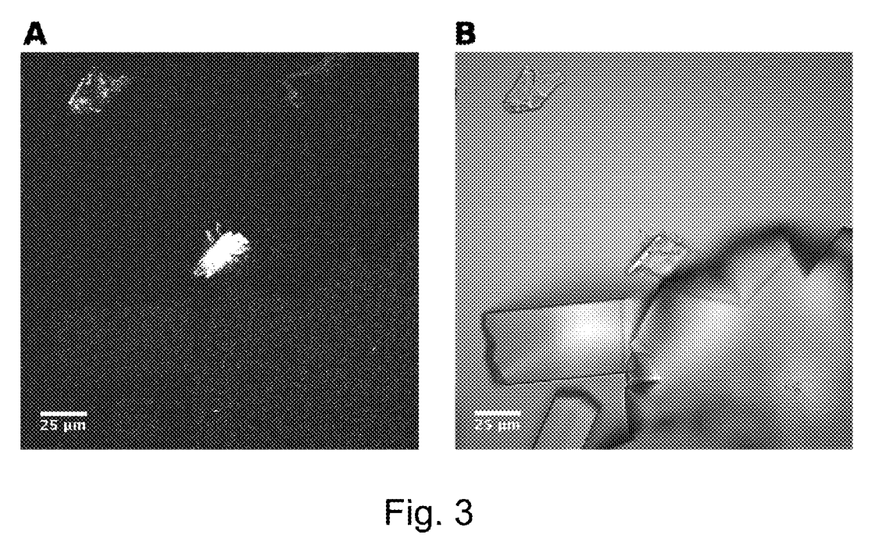
FIG. 3A is a SHG micrograph of lysozyme crystals.
FIG. 3B is a bright field image corresponding to FIG. 3A.

The use of epi-detection in the second harmonic generation microscopy measurements of lysozyme likely also contributed to the relatively small S/N generated from the larger lysozyme crystals. The data in FIG. 3 were acquired in an epi-detection configuration. However, crystals with thicknesses significantly exceeding the wavelength of light can be expected to generate primarily forward-propagating second harmonic generation, away from the detector. Therefore, large crystals as shown in FIG. 3 should yield relatively weak signals as second harmonic generation is expected to be generated predominately in the forward direction.

Finally, the surface itself may play a role in orienting the lysozyme crystals relative to the direction of propagation of the beam. All microscopy measurements were performed with the k-vector of the beam incident normal to the glass surface upon which the lysozyme crystals were grown. Because the only symmetry-allowed nonzero elements for this polymorph of lysozyme are $\chi_{XYZ} = \chi_{XZY} = \chi_{YXZ} = \chi_{YZX}$, no second harmonic generation can arise if the beam is propagating directly along a crystallographic axis. The measurements shown in FIG. 2 confirm that similarly prepared lysozyme crystals generate much stronger second harmonic generation-activity when the substrate plane is tilted relative to the beam propagation axis.

The intrinsically low second harmonic generation activity of lysozyme coupled with the use of epi-detection in a direction likely along a crystallographic axis collectively explain the relatively weak responses observed for the larger lysozyme crystals. These same explanations are also consistent with the observed maxima in second harmonic generation in the lysozyme micrographs from polycrystalline conglomerates and from defects within the lysozyme lattice. In both cases, the factors that conspired to reduce the second harmonic generation activity of macroscopic crystals are relaxed. Polycrystalline domains are more likely to be relatively small and therefore efficient generators in the epi-detection configuration. Furthermore, the absence of surface templating allows the crystalline domains to adopt more favorable orientations relative to the beam axis.

The $his_8$-GFPuv pT7-7 plasmid was a generous gift from Dinesh Yernool, Purdue University. The $his_8$-GFPuv plasmid (50 μg) was transformed into 50 μL XL1-blue cells (Invitrogen), which were incubated on ice for 30 minutes. The cells were heat-shocked at 42° C. for 45 s, cooled on ice for 2 min, then added to 1 mL 2×YT media and incubated at 37° C. for 1 h. The cells were collected by centrifugation at 14000 rpm for 5 minutes and the cell pellet was resuspended in 200 μL 2×YT media. The cells were plated on agar plates treated with 100 μg/mL ampicillin and incubated at 37° C. overnight. One colony was added to 10 mL 2×YT media treated with 100 μg/mL ampicillin and incubated with shaking at 37° C. for 4 h. The plasmid was extracted using the Wizard Plus SV Miniprep kit (Promega). The purity of the DNA was checked using the $Abs_{260}/Abs_{280}$ ratio after extraction. The plasmid was transformed into BL21(DE3) cells (Invitrogen) by adding 1 μL of the plasmid to 50 μL cells and incubating on ice for 30 min. The cells were heat-shocked at 42° C. for 45 s, cooled on ice for 2 min, then resuspended in 1 mL 2×YT media. The cells were shaken at 37° C. for 1 h and collected by centrifugation. The cell pellet was resuspended in 1 mL 2×YT media and the cells were plated onto agar plates treated with 100 μg/mL ampicillin. The plates were incubated at 37° C. for 12 h. One colony was added to 10 mL 2×YT media treated with 100 μg/mL ampicillin and were shaken at 37° C. until the $OD_{600}$ reached 0.8.

Next 1 mL of the 10 mL culture was added to 1 L of 2×YT treated with 100 μg/mL ampicillin. The cells were shaken at 37° C. until the $OD_{600}$ reached 0.5-0.8. The cells were induced using 1 mM isopropyl-β-D-thiogalctopyranoside and shaken at 37° C. until the $OD_{600}$ reached 1.6. The cells were collected by centrifugation at 13,500 rpm for 10 min. The cell pellets were checked for green fluorescence using a hand-held UV lamp before proceeding. The cell pellets were combined and resuspended in 50 mL binding buffer for purification (10 mM imidazole, 300 mM NaCl, 50 mM $NaH_2PO_4$, pH 8.0). The cells were French pressed until the solution was homogeneous and collected by centrifugation at 18000 g for 45 min. The supernatant was filtered through 0.2 μm membrane filters and loaded onto a HisTrap HP column (GE Life Sciences) at 4° C. using an AKTA Prime fast performance liquid chromatography system (GE Life Sciences) for purification. Immediately before purification the binding and elution buffer (250 mM imidazole, 300 mM NaCl, 50 mM $NaH_2PO_4$, pH 8.0) were treated with 1 mM PMSF (phenylmethanesulfonylfluoride) and 0.5 mM DTT (dithiothreitol). The protein was eluted using 250 mM imidazole and the fractions containing the protein were pooled. The pooled fractions were dialyzed twice using regenerated cellulose membranes (12 kDa cutoff, Spectra/Por) against phosphate buffered saline, pH 7.4. The fractions were characterized using 12.5% acrylamide SDS-PAGE gel electrophoresis and Western blot analysis. For Western blot analysis the SDS-PAGE gels were transferred onto nitrocellulose membranes on ice for 1.5 h at 100V. A Ponceau S stain was used to confirm the transfer of protein onto the membrane. The membranes were rinsed three times with tris-buffered saline with 1% Tween-20 (TBS/T). The membranes were blocked with 5% milk for 1 h at room temperature, rinsed three more times with TBS/T, and treated with a 1:5000 dilution of the primary antibody, either rabbit anti-his6 IgG or rabbit anti-GFP IgG (Abcam). The membranes were rinsed three times with 0.5% milk and treated with the secondary antibody, horseradish peroxidase-anti-rabbit IgG (eBioscience) at a 1:20,000 dilution for 35 min. The membranes were rinsed three times with TBS/T and incubated with 1:1 A:B reagents (Supersignal West Pico Chemiluminescent Substrate, Pierce) for 1 min. The blots were exposed to CL-Xpose Film (Pierce) for detection for 30 s-1 min. The final protein concentration was determined using a microBCA Protein Assay Kit (Pierce).

Lysozyme from chicken egg white was obtained from Sigma. Crystals were prepared using a standard procedure. (McPherson, A., *Crystallization of biological macromolecules*. Cold Spring Harbor Laboratory Press: New York, 1999) Crystallization was performed using the batch method between two glass cover slips (untreated) separated by an o-ring. Grease was used to obtain an air tight seal. These crystals were tetragonal in symmetry, belonging to the space group $P4_32_12$.

Second harmonic generation measurements were taken using several systems. Transmission measurements incidence angles of 0° and 45° were performed using nanosecond pulses of 1064 nm light from a Nd:YAG laser with a 20 Hz repetition rate. The incident light was p-polarized. Lysozyme crystals were imaged using a mode-locked Ti:Sapphire laser (Mai Tai, Spectra Physics) at 840 nm with a pulse width of 130 fs and a repetition rate of 77 MHz. The laser beam was directed into a scanning confocal microscope (FV1000, Olympus Inc.) with a 60× water-immersion objective (NA=1.2). A second second harmonic generation microscope system was also employed, consisting of an 80 MHz mode-locked Ti:Sapphire laser (KML, 40 fs, ~50 mW) directed into a Nikon eclipse TE-2000U microscope (10×, 0.3 N.A.). The beam was translated horizontally in the field of view by a resonant vibrating mirror operating at 7.8027 kHz, with the slow-scan motion actuated by an automated translation stage. A 400 nm dichroic mirror directed the epi-detected second harmonic generation toward a photomultiplier (PMT) following passage through an IR-blocking filter and a bandpass filter centered at 400 nm. The rest of the light was directed toward a PMT with a bandpass filter centered at 532 nm for epi-detection of TPEF. The transmitted second harmonic generation was collected with an objective (10×, 0.25 N.A.) and directed toward a PMT using a similar optical path as in the epi-detection arrangement. The time-dependent accumulated photon counts from $10^5$ oscillations of the vibrating mirror were used to reconstruct each slow-scan line, the collective set of which was subsequently compiled into an 8-bit grayscale image and digitally adjusted to overlay with the bright-field image.

From the forgoing description of the structure and operation of a preferred embodiment of the present invention, it will be apparent to those skilled in the art that the present invention is susceptible to numerous modifications and embodiments within the ability of those skilled in the art and without exercise of the inventive facility. Accordingly, the scope of the present invention is defined as set forth of the following claims.

The invention claimed is:

1. A method of detecting a protein crystal comprising:
   subjecting a sample comprising a protein crystal to second order nonlinear optical imaging; and
   detecting a second harmonic generation signal produced by the protein crystal suitable for protein structure determination by diffraction analysis.

2. The method of claim 1, wherein the protein crystal has a diameter of less than about 1 micron.

3. The method of claim 2, wherein the diameter is less than about 100 nm.

4. The method of claim 1, further comprising:
   illuminating the sample with a pulsed laser light.

5. The method of claim 4, wherein the laser light is pulsed at less than about one picosecond.

6. The method of claim 1, wherein the sample is formed from a crystallization experiment.

7. A method for evaluating protein crystal quality for structure determination by diffraction analysis comprising:
   subjecting a sample comprising a protein crystal to second order non-linear optical imaging;
   detecting a second harmonic generation signal produced by the protein crystal;
   comparing a forward second harmonic generated signal and a backward second harmonic generated signal of the protein crystal; and
   selecting a protein crystal exhibiting a predominately forward scattering for use in crystallography.

8. The method of claim 7, further comprising, selecting the protein crystal for use in crystallography wherein the forward second harmonic generated signal is between about 4 times and about 6 times greater than the backward second harmonic generated signal.

9. The method of claim 8, wherein the forward second harmonic generated signal is about 5 times greater than the backward second harmonic generated signal.

10. The method of claim 7, wherein the diameter of the protein crystal is less than about 1 micron.

11. The method of claim 10, wherein the diameter of the protein crystal is less than about 100 nm.

12. The method of claim 7, further comprising illuminating the sample with a pulsed laser light.

13. A method for evaluating protein crystal quality for structure determination by diffraction analysis comprising:
   subjecting a sample comprising a protein crystal to second order non-linear optical imaging;
   illuminating the protein crystal with a pulsed laser beam at a first incidence angle;
   detecting a second harmonic generation signal produced by the protein crystal at the first incidence angle;
   rotating the protein crystal to a second incidence;
   detecting a second harmonic generation signal produced by the protein crystal at the second incidence angle; and
   comparing the second harmonic generation signal produced by the protein crystal at the first and second incidence angle.

14. The method of claim 13, further comprising
   measuring the intensity of the second harmonic generation signal produced by the protein crystal at the first incidence angle;
   measuring the intensity of the second harmonic generation signal produced by the protein crystal at the second incidence angle;
   comparing the intensity of the second harmonic generation signal produced by the protein crystal at the first and second incidence angle; and
   selecting a protein crystal exhibiting a lower minimum intensity for use in crystallography.

15. The method of claim 13, wherein the diameter of the protein crystal is less than about 1 micron.

16. The method of claim 15, wherein the diameter is less than about 100 nm.

17. A method for evaluating a crystallization experiment comprising:
   subjecting a protein crystallization experiment to second order non-linear optical imaging; and
   using a second harmonic generation signal to evaluate whether a protein crystal suitable for protein structure determination by diffraction analysis is present in the crystallization experiment.

18. The method of claim 17, wherein the protein crystal has a diameter of less than about 1 micron.

19. The method of claim 18, wherein the diameter is less than about 100 nm.

20. The method of claim 17, further comprising illuminating the crystallization experiment with a pulsed laser beam.

* * * * *